(12) United States Patent
Schummers

(10) Patent No.: US 8,077,944 B2
(45) Date of Patent: Dec. 13, 2011

(54) METHOD, DEVICE, AND COMPUTER PROGRAMME FOR EVALUATING IMAGES OF A CAVITY

(75) Inventor: Georg Schummers, Munich (DE)

(73) Assignee: TomTec Imaging Systems GmbH (DE)

( * ) Notice: Subject to any disclaimer, the term of this patent is extended or adjusted under 35 U.S.C. 154(b) by 506 days.

(21) Appl. No.: 12/064,269

(22) PCT Filed: Jun. 8, 2007

(86) PCT No.: PCT/EP2007/005094
§ 371 (c)(1),
(2), (4) Date: Feb. 23, 2009

(87) PCT Pub. No.: WO2007/141038
PCT Pub. Date: Dec. 13, 2007

(65) Prior Publication Data
US 2009/0175515 A1   Jul. 9, 2009

(30) Foreign Application Priority Data
Jun. 8, 2006   (DE) .......................... 10 2006 026 695

(51) Int. Cl.
*G06K 9/36* (2006.01)
*A61B 5/04* (2006.01)
(52) U.S. Cl. ........ 382/128; 382/131; 382/173; 600/427; 607/4

(58) Field of Classification Search .......... 382/128–131; 600/407–464
See application file for complete search history.

(56) References Cited

U.S. PATENT DOCUMENTS

| | | | |
|---|---|---|---|
| 6,389,310 B1 | 5/2002 | Demonceau et al. | |
| 7,379,532 B2 * | 5/2008 | Kramp | 378/108 |
| 7,668,370 B2 * | 2/2010 | Noble et al. | 382/173 |
| 2002/0072672 A1 * | 6/2002 | Roundhill et al. | 600/450 |
| 2005/0008209 A1 | 1/2005 | Matsumoto | |
| 2005/0020903 A1 | 1/2005 | Krishnan et al. | |
| 2005/0027193 A1 * | 2/2005 | Mitschke et al. | 600/427 |
| 2005/0143777 A1 * | 6/2005 | Sra | 607/4 |

FOREIGN PATENT DOCUMENTS

| | | |
|---|---|---|
| DE | 69809538 | 3/1998 |
| EP | 1070480 | 7/2000 |
| WO | 01/01859 | 1/2001 |
| WO | 2004/003851 | 1/2004 |
| WO | 2004/097720 | 11/2004 |

* cited by examiner

*Primary Examiner* — Melissa Koval
*Assistant Examiner* — Emily Chan
(74) *Attorney, Agent, or Firm* — Cantor Colburn LLP

(57) ABSTRACT

The invention relates to a device, a method and a computer program for evaluating images of the heart that have been captured by means of a medical imaging method. According to said method, at least two data records containing functional values, which describe the ventricular wall activity, are produced in a random format, are converted into a uniform format and the data records in the uniform format are compared with one another or calculated.

17 Claims, 3 Drawing Sheets

| Sektor | Kontraktions-zeit | maximale Volumen-änderung | Verzögerung |
|---|---|---|---|
| 1 | 170 ms | 52 % | 0 ms |
| 2 | 200 ms | 42 % | 30 ms |
| 3 | 210 ms | 20 % | 40 ms |
| 4 | 190 ms | 50 % | 20 ms |
| ⋮ | ⋮ | ⋮ | ⋮ |

Ruhe    Belastung    Differenz

US 8,077,944 B2

METHOD, DEVICE, AND COMPUTER PROGRAMME FOR EVALUATING IMAGES OF A CAVITY

FIELD OF THE INVENTION

The invention relates to a method of evaluating images of a cavity in the human or an animal body, which have been acquired with medical imaging methods such as real-time 3D ultrasound, X-ray methods, computer tomography (CT), magnetic resonance tomography (MRT), an electrophysiological cardiac catheterisation examination, or nuclear-medical methods such as Positron Emission Tomography (PET) or Single Proton Emission Computed Tomography (SPECT). In particular, the images are dynamic images, i.e. images taken consecutively in a time sequence. The evaluation is preferably not carried out on the images directly, but on data sets with functional values which have been obtained or computed from the images.

BACKGROUND OF THE INVENTION

Currently various imaging means or methods are used to assess functional disturbances, which allow the acquisition of dynamic three-dimensional images, e.g. ultrasound, magnetic resonance tomography (MRT), Positron Emission Tomography (PET) or Single Proton Emission Computed Tomography (SPECT). "Dynamic" is intended to mean that a time sequence of images is acquired, which, for example, allows visualisation of the movement of the heart. Particularly suitable for this are real-time 3D ultrasound systems with which real-time images can be acquired in 3D.

During one exemplary functional evaluation, the wall of a cavity, such as the heart chamber, is observed and its movement is followed. A disturbance e.g. of the heart muscle activity can be detected, for example, in that the heart chamber wall is not contracting simultaneously everywhere and not everywhere with the same strength. This can be determined by automatically detecting and observing the contours of the chamber (e.g. the left or right ventricle or an atrium). The inner wall of the cavity can then be represented as a type of grid network structure (as was described for example in EP 0 961 135 by the Applicant) whose surface is approximated, for example, by triangles (such grid network structure is referred to below as "pouch"). The pouch is then divided into sections, and the movement of the individual sections is followed in order to determine, for example, the contraction time and respective delay times compared to the section with the earliest contraction. The cavity (e.g. of the heart) can also be divided into volume sections, whose change in volume e.g. over a heartbeat is observed. The results of such evaluations are often represented in the form of what is known as a "polar plot", which e.g. shows the heart spread out as on a flat land map, in which a sector in the polar plot is allocated to each section of the heart chamber wall. A polar plot therefore represents virtually a flat map e.g. of a heart chamber, on which certain functional values such as contraction time or maximum volume change are applied in a color-coded manner.

Such evaluations are carried out, for example, with the software programs TomTec Left Ventricular Analysis, TomTec Right Ventricular Analysis and 4D Left Ventricular Analysis Cardiac Resynchronization Therapy and e.g. with PET/SPECT softwares. The evaluation methods used in these programs for obtaining data sets with functional values are described for example in the following articles:

Kapetanakis, Monaghan L: "Real-Time Three-Dimensional Echocardiography—A Novel Technique to Quantify Global Left Ventricular Mechanical Dyssynchrony", Circulation. 2005; 112:992-1000.

Bax J J, Abraham T, Barold S S, Breithardt O A, Mark D B, Monaghan M G, Nihoyannopoulo: "Cardiac resynchronization therapy: Part 1—issues before device implantation", J Am Coll Cardiol. 2005 Dec. 20; 46 (12):2168-82.

Monaghan M J: "Role of real time 3D echocardiography in evaluating the left ventricle", Heart. 2006 January; 92(1): 131-6.

Lipiec P, Piewka M, Kasprzak J D: "Automated quantification of left-ventricular volumes and function: a novel clinical tool?" Congress of the European Society of Cardiology 2003.

The results of such evaluations are then transmitted as a multidimensional data set with functional values, e.g. in the form of a pouch which can be built up from points, triangles, or the like and may additionally contain functional values, as a polar plot or as a data table.

A cardiologist is often faced with having to compare different functional evaluations of the heart chambers with one another, e.g. in a stress echo test, in which functionally disturbed areas in the myocardium of the left ventricle are evaluated at rest and during stress of the patient. In clinical routine a comparison between the resting and the stressed state has hitherto been always carried out by subjective assessment by the doctor. Occasionally, data obtained by different imaging means must be compared with one another, e.g. a perfusion image of the heart obtained by PET or SPECT with a dynamic data set showing the activity of the heart chamber wall.

A standardised, qualitative comparison is only available on the basis of 2D sections of the heart. This standard was developed by the American Congress of Cardiology (ACC) and by the American Heart Association (AHA). However, this method only offers very limited spatial scanning of the left ventricle, since only a few specified 2D sections (three long axis sections and one short axis section) are assessed by the observer and not the whole ventricle. The findings are therefore not easily comparable because of their intra- and inter-observer-variability.

In the prior art, therefore, no methods for evaluating dynamic images, e.g. of the heart, are available which permit complete spatial comparative evaluation and hence provide an objective medical finding. With the different formats in which the functional evaluations of the heart chambers are made available, there is no possibility for considering different examination results at a glance.

SUMMARY OF THE INVENTION

The invention therefore has the object of providing a method of evaluating images of a cavity in the human or an animal body which overcomes the above-mentioned disadvantages.

This object is achieved by the invention with the features of claim 1. Advantageous embodiments of the invention are indicated in the subclaims.

The invention is characterised in that at least two data sets with functional values are made available each in a different data format, in particular in the form of a data table, a projection onto a 2D plane (e.g. a polar plot) or a grid network structure (e.g. a pouch data set). The data sets with functional values are to be compared, e.g. with one another. Each data set is preferably obtained or computed from a set of images of the cavity acquired with a specified imaging method. The invention is further characterised in that a uniform data format is provided, in particular is selected by a user, wherein the data set(s) with functional values not made available in this uniform data format are converted into the uniform data format; wherein the data sets then available in the uniform data format are computed at least once with one another (e.g. added or subtracted) to generate at least one result data set; and finally the result data set is displayed.

Preferably, the cavity is a chamber of the heart, e.g. the left ventricle, the right ventricle, the left or right auricle (atrium), or another blood vessel such as the aorta. The invention may, however, also be applied to other cavities such as the intestine, the stomach, a ventricle of the brain, the bladder etc.

The data sets with functional values (referred to below as "functional data sets") have each been obtained or computed from images of the cavity, which have been acquired with a medical imaging method. The expression "images of the cavity" is in this case to be taken very comprehensively, and may mean also measurement data not directly present in image form after acquisition, e.g. the results of a scan of the heart chamber wall with an electrode, which supplies a spatial distribution of the electrical potential. Since these measurement data also contain spatial information, they are also to be understood as "images" in the widest sense. From the images of the potential, a functional data set can be obtained, which reproduces the electrical potential in the scanned sections of the heart chamber wall.

The "images of the cavity" may further be the results of a perfusion measurement carried out e.g. with a nuclear-medical method such as PET or SPECT. The functional data set so obtained thus contains blood circulation values for plural sections of the heart chamber wall. Since the spatial resolution of PET and SPECT is low, the individual sections of the heart chamber wall to which a perfusion value is allocated are very large.

The "images of the cavity" may also be two-dimensional (2D), three-dimensional (3D) or four-dimensional (4D) images which have been acquired by MRT, X-ray, CT or ultrasound. A 4D image is a sequence of 3D images taken consecutively in a time sequence. If the cavity is a heart chamber, a 4D image then preferably covers one heart cycle.

"Images of the cavity" which are particularly preferred are 4D ultrasound images. From these images, numerous different data sets with functional values can be determined, in particular those which are associated with the movement of the heart chamber wall, e.g. the maximum relative displacement of the heart chamber wall, the time delay of the maximum displacement of the heart chamber wall, the change in volume of a section of the heart chamber during a heart cycle, the thickness of the heart chamber wall, strain, strain rate etc. The strain of a muscle is the ratio of the momentary length to the maximum (relaxed) length of the muscle and can be calculated from the change in heart chamber wall thickness during a heart cycle.

Thus the images of the cavity may be either static (in the case of the heart e.g. acquired with ECG-triggering), or dynamic, i.e. time-dependent. Thus the functional data sets may also either contain values which remain the same over a heartbeat (e.g. the change in volume during a heart cycle) or dynamic values such as the momentary movement of the heart chamber wall.

Therefore, it can be concluded that different data sets with functional values which have been obtained from images of different imaging modalities, or which have been determined in different ways from the images of the cavity, may be present in completely different data formats. Although the functional data sets all generally contain spatial information relating to the functional values, they may have different coordinate systems and resolutions. The data sets with functional values are preferably multidimensional, in particular two- or three-dimensional, but may also be one-dimensional.

The functional values to be compared may, for example, represent the movement of the heart chamber wall, the relative displacement of the heart chamber wall, the time delay of the maximum displacement of the heart chamber wall, the volume change of a section of the heart chamber, strain, strain rate, perfusion, electrical potential, and mathematical derivatives thereof, each for a section of the heart chamber wall.

The functional values may be both scalars and vectors, a vector value being, for example, the movement of the chamber wall (direction of motion and maximum speed) or may represent the electrical activation of the chamber wall (direction and size of an action potential).

The invention therefore permits any comparison or computation/reconciliation of functional data sets which are available in different data formats, e.g. in the form of pouch data, polar plots or data tables. In this case, a uniform data format is used, into which the other data sets are converted. The uniform data format is either established in advance or is selected by a user for a particular analysis. The uniform data format may also be a format in which one or more of the functional data sets are already available. Most preferred, the uniform data format is a polar plot or a pouch data set, as described in EP 961 135 A.

In converting the functional data sets into the uniform data format, the different coordinate systems of the data sets are placed in relation to one another and converted to one another, e.g. Cartesian coordinates are converted into polar coordinates and vice versa. This is made possible by the reference system common to all data sets of the cavity—generally all data sets contain values which are allocated spatially to the walls of the cavity, so that the coordinate systems of the data sets can be mapped onto one another in this manner. If, for example, in one functional data set values for the electrical potential of the heart chamber wall are given with a spatial reference (x; y; z) to the Cartesian 3D system, from this polar coordinates can be computed for a polar plot, provided—e.g. in the case of the left ventricle—the position of the apex and of the mitral annulus (the upper limit of the left ventricle) is known in the 3D system.

Preferably, in the conversion, the different spatial resolutions of the functional data sets are also taken into account. For example, data sets with low spatial resolution are oversampled or interpolated in order to achieve a higher spatial resolution. The data sets with a high spatial resolution are under-sampled or plural data points are averaged in order to gain a lower spatial resolution. In this process interpolation and approximation processes can be used.

After conversion into the uniform data format, the functional data sets are computed with one another in order to evaluate them or to compare them with one another. This is done preferably by computing or reconciling each data point of a first functional data set with the data point of the second or further data sets which corresponds to the spatial position of the data point of the first functional data set, e.g. by subtracting, adding, multiplying, or dividing one with the other, or by combinations of these operations. It is also possible to take a derivation and to integrate e.g. over plural data sets which have been obtained from images which are consecutive in time.

Computation can also be carried out on the basis of a model, i.e. in computing, mathematical models of the cavity can be taken into account, e.g. the curve of excitation lines in the heart chamber wall, in order to compute the input data with one another. The curve of the excitation lines in the heart wall may e.g. be measured or computed from other data. In computing two functional data sets with each other, the excitation lines are then "placed one over another" by a spatial imaging function, which means that the spatial sections which have the same relative position to the excitation lines are compared to one another.

Therefore, in model-based computation not only are points which have the same position in space computed with one another, but also those between which, e.g. a physiological association exists, are computed with one another. Thus, functional evaluations of, e.g. the heart chambers, can be quantitatively compared in at least one complete spatially comparative evaluation.

Preferably, this is because the data sets with functional values contain functional values spatially resolved for all or almost all sections of the cavity. For example, the movement of the heart chamber is not only compared locally in two or three section images, but if possible over the entire area or volume of the compared data. To this end, a projection onto a 2D plane such as a polar plot may, for example, be chosen as a uniform format. If some of the data sets with functional values are in another format, e.g. as a pouch data set or in the form of a data table, these are transferred into a uniform data format, e.g. into a polar plot.

If necessary, further calculations are carried out, e.g. averaging over the section of a pouch-data set corresponding to a sector of the polar plot, or calculating the position in the polar plot of each point on the pouch.

Particularly preferably, the at least two data sets with functional values have been obtained from dynamic images of the heart, which have been acquired in different states of stress of the heart. For example, a typical stress echo examination is carried out at rest, during light physical stress, and during severe physical stress.

Alternatively, the invention can also be used to compare images of the heart which have been taken using different imaging methods or means, e.g. with MRT and ultrasound or with PET and ultrasound. The method can also be used for comparing data sets with functional values which have been acquired by means of computer tomography (CT), magnetic resonance tomography, catheter examinations (e.g. measurement of potential), PET or SPECT. In this respect, the method can also be used on non-imaging methods such as electrophysiological cardiac catheterisation examination (measurement of potential in the heart).

According to a particular embodiment, the images of the cavity and/or the data sets with functional values may be a dynamic time sequence of three-dimensional image data sets.

If the data sets have not been brought to the same spatial resolution (pixel size) in the conversion to the uniform data format, the functional data sets can still be computed with one another. In this case the functional data sets are over- or under-sampled, as necessary, if they are available in different spatial resolutions.

The representation/display of the result data sets can take place in different ways. For example, all original and computed polar plots or pouch data sets can be represented side-by-side. Optionally, plural polar plots can also be shown one over another (semi-transparent), in which case for example a slidable window is provided in the upper polar plot, through which the lower polar plot is visible. Furthermore, it is possible to show all original and/or reconciled values on a pouch representation of the heart chamber colour-coded, for example.

To this end, the values of the three stress echo data sets computed and exported, for example in the program "4D LV analysis CRT" of the Applicant, are loaded and computed with one another. In this case, for example, the differences of the respective values between the three data sets are calculated and again shown as a parameter map in a polar plot or on a pouch.

As one embodiment of the computation, a Boolean operation (e.g. AND, OR, and NOT) is carried out. This is particularly suitable for functional values which can be reduced to binary values (0 or 1). For example, the perfusion after an infarction in one section of the heart chamber wall under stress may drop to zero. This information can be combined with other values, e.g. detected movement of this section, in order to identify a permanently damaged area of the heart. The link with Boolean operators is also suitable in terms of time, e.g. to visualise movement patterns. To this end, e.g. the symmetrical difference (set union without intersection/cut set) of two pouches is formed in order to show position differences in space.

The invention is also directed to a computer program product which contains program code stored on a computer-readable medium, wherein the program code effects carrying out the above-described method when the program code is run on a computer.

Finally, the invention also relates to a device for evaluating images of a cavity, e.g. of the heart, which have been acquired with a medical imaging method, the device being adapted, in particular, to carry out the method described above. To this end, the device comprises: a data store, in which data sets with functional values are stored which describe, e.g. the heart chamber wall activity of a heart chamber, and which have been computed from the images of the cavity, in which case at least two data sets with functional values are supplied in any data format, in particular in the form of a data table, a projection onto a 2D plane, or a grid network structure in the data store; a computing unit, which is adapted to convert the data set(s) with functional values not made available in a uniform data format into a uniform data format, compute the data sets present in the uniform data format with one another (e.g. to add or subtract), and generate at least one result data set; and a screen suitable for displaying the result data set.

BRIEF DESCRIPTION OF THE DRAWINGS

The invention will now be explained more fully with the aid of embodiments and with reference to the attached drawings, which show.

DETAILED DESCRIPTION OF THE DRAWINGS

Figure 1:
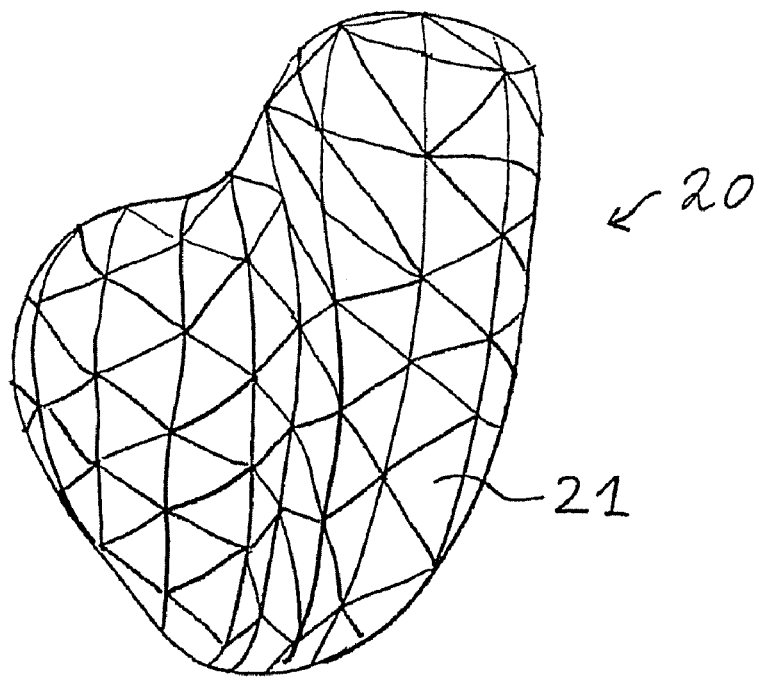
FIG. 1 a pouch data set.

FIG. 1 illustrates the pouch format in which the functional values may be presented. This data format is described in detail in EP 0 961 135 A, the disclosure of which is incorporated into this application by reference. This involves a geometric grid network structure similar to a pouch 20, which is represented by individual points or, as in the example shown, by individual triangles 21. A pouch 20 of this type may be derived from a three-dimensional image data set of a cavity, e.g. by determining the contours between the interior and wall of the cavity. In the case of a heart chamber, preferably the interface between blood and wall is contoured, the interface between wall and surrounding tissue can optionally be contoured in addition. By the contouring, a surface is obtained, which is then parameterised. For the pouch format, individual points or triangles are extracted which span a pouch and are given in Cartesian coordinates (3D or 4D) or in spherical coordinates. A dynamic 3D data set may thus be represented by a dynamic pouch data set, i.e. one that changes over time. Additionally, functional values can be determined from the dynamic pouch data set, e.g. the moment of contraction or the like and be represented as a coloured area on the pouch 20.

Figure 2:
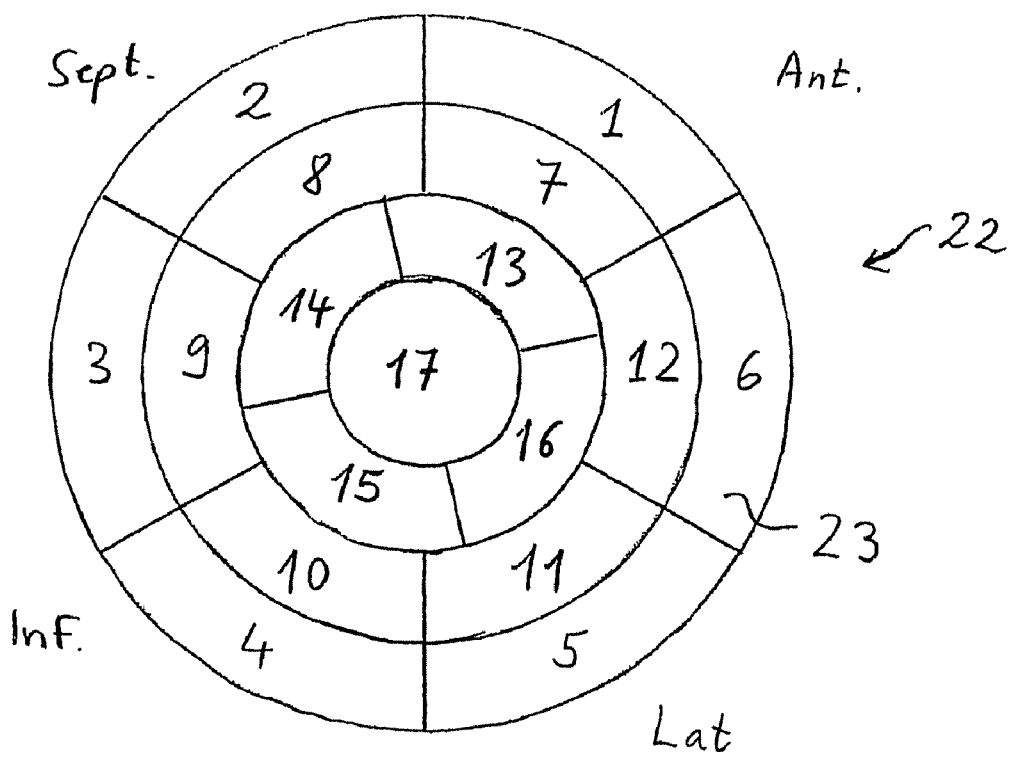
FIG. 2 a polar plot.

An alternative form of representation is the polar plot 22, which is shown in FIG. 2. The polar plot is a representation e.g. of the heart chamber wall projected according to certain rules onto a 2D plane, the projection being divided into plural sectors 23. Sector 17 lies at the tip (e.g. on the apex) of the pouch for example, and the sector 1 at the anterior end of the chamber. Also a polar plot can be derived from a 3D image of the heart by contouring the interface between blood and wall. The position of the apex is determined and the derived surface is parameterised by computing for each desired point of the surface the two angles relative to the apex (origin of the coordinate system). This in itself allows representation as a polar plot. If necessary, the distance from the origin is also determined A polar plot can have any high or low spatial resolution.

The polar plot can be used to represent various functional values, e.g. the time delay of the contraction or the maximum volume change in each sector. Additionally, the individual values are again colour-coded and applied as a map to the polar plot.

Figures 3, 4:
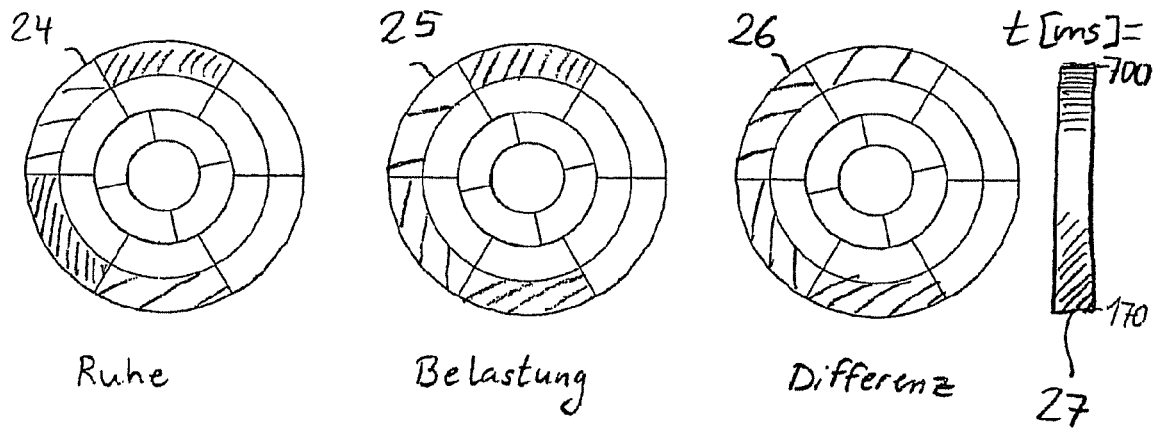
FIG. 3 a data table.
FIG. 4 an embodiment of the representation of original and result data sets.

A further alternative for representing functional values for the heart chamber wall activity is shown in FIG. 3, in particular a data table. This data table is also arranged according to spatially defined areas (depending on resolution which may be as high as pixel level). The advantage of a data table is that various functional values, in this case for example the contraction time, maximum volume change and delay in ms, can be shown simultaneously. The disadvantage is that no visualisation takes place and the results cannot therefore be detected at a glance.

According to one embodiment of the method according to the invention, it is now possible to convert the data sets with functional values present in the three different formats respectively into a uniform format, e.g. into a polar plot, and then to compare them with one another. For example, from the data table in FIG. 3, a polar plot according to FIG. 2 is determined by means of the numbers of the sectors, which however has a lower resolution than other polar plots. In a polar plot according to FIG. 2, each pixel in one sector does not have to have the same value. Furthermore, the functional values visualised on a pouch can also be converted into a polar plot. In this manner, direct comparison of various types of data is possible.

In FIG. 4 for example, a corresponding representation of the result data sets is shown. Here, 24 represents a polar plot of the left ventricle at rest. In the polar plot, for example, the contraction times are shown in color in ms, according to the color scale 27. The polar plot 25 represents the same functional value in the stressed state. Polar plot 26 shows the result data set, in this case a differential between the data sets of the polar plots 24 and 25. For the polar plot 26, a different color scale may apply than for the other two plots. If the representation is shown on a monitor with computer terminal, the user can also scan the comparative value determined at each point, for example by passing a mouse over the polar plot 26.

The result data sets thus obtained are objective and not dependent on the observer, unlike conventional evaluation. Therefore, they are also usable in progression studies.

Figure 5:
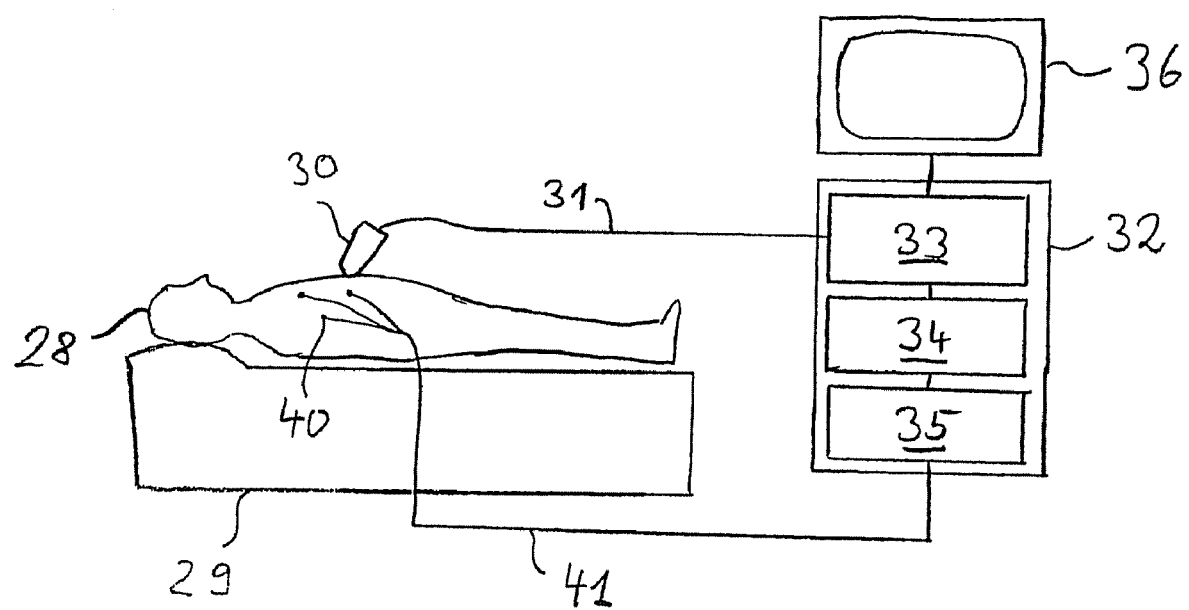
FIG. 5 an embodiment of a device according to the invention.

In FIG. 5 an embodiment of a device according to the invention is shown. There, a patient 28 is positioned on a couch 29. Ultrasound images, e.g. of the heart, are acquired with the ultrasound probe 30 and transmitted via the cable 31 to the evaluation unit 32. The unit 32 comprises a computer unit 33 and a data store 34. Furthermore, an optional ECG apparatus 35 can be provided. This is connected via a cable 41 to plural electrodes 40, with which during the ultrasound image acquisition an ECG can be taken. This simplifies the allocation of the acquired images to specific phases of the heart cycle.

The method according to the invention may, for example, be carried out by the computing unit 33 directly after acquisition of the dynamic images. To represent the result data sets, a screen 36 is provided.

KEY TO DIAGRAMS

FIG. 3
Sektor—sector
Kontraktionszeit—contraction time
Maximale. —maximum volume change
Verzögerung—delay
FIG. 4
Ruhe—rest
Belastung—stress
Differenz—differential

The invention claimed is:

1. Method of evaluating images of a cavity in a human or an animal body, which have been acquired with one or more different medical imaging methods,
    wherein data sets with functional values, computed from said images, are used, the method comprising the steps of:
        providing at least two data sets with functional values in different data formats, wherein the data formats are chosen from the group consisting of a data table, a projection on to a 2D plane, or a grid network structure;
        providing a uniform data format;
        converting a data set with functional values not made available in the uniform data format into the uniform data format;
        Mathematically computing data sets present in the uniform data format with one another to generate at least one result data set; and
        representing the result data set.

2. Method according to claim 1, wherein the cavity is a heart chamber.

3. Method according to claim 2, wherein the data sets with functional values each represent functional values for plural spatial sections of the heart chamber chosen from the group consisting of movement of the heart chamber wall, relative displacement of the heart chamber wall, time delay of a maximum displacement of the heart chamber wall, volume change of a section of the heart chamber, wall thickness, perfusion, strain, strain rate, or electrical potentials of the heart chamber wall.

4. Method according to claim 1, wherein the uniform data format is a polar plot.

5. Method according to claim 1, wherein a mathematical computation of data sets present in the uniform format is chosen from the group consisting of adding together, subtracting from one another, or combining the data sets with one another by Boolean operators.

6. Method according to claim 1, wherein the images of the cavity are at least in part dynamic images.

7. Method according to claim 6, wherein the images of the cavity and/or the data sets with functional values are a time sequence composed of three-dimensional image data sets.

8. Method according to claim 2, wherein the images of the heart chamber are 4D stress echo image data sets.

9. Method according to claim 2, wherein the data sets with functional values contain functional values resolved spatially to all or almost all sections of the cavity.

10. Method according to claim 2, wherein the at least two data sets with functional values have been obtained from images of the heart, which have been acquired in different states of stress of the heart.

11. Method according to claim 1, wherein the at least two data sets with functional values have been obtained from images of the cavity which have been acquired with different medical imaging methods.

12. Method according to claim 1, wherein the images of the cavity have been acquired by means chosen from the group consisting of ultrasound, X-ray, Computer Tomography, Magnetic Resonance Imaging, electrophysiological catheter test, Positron Emission Tomography or SPECT.

13. Method according to claim 1, wherein the at least two data sets composed of functional values are converted into a uniform format, but with different spatial resolution, wherein during computation of the data sets present in the uniform format, data set(s) with a lower spatial resolution are over-sampled and/or data set(s) with a higher spatial resolution are under-sampled.

14. Method according to claim 1, wherein the result data sets are represented in a projection on to a 2D plane.

15. Computer program product embodied on a non-transitory computer readable medium, which contains program code stored on a computer-readable medium, which performs the method according to claim 1 if the program code is executed on a computer.

16. Device for evaluating images of a cavity in a human or an animal body, which have been acquired with one or more medical imaging methods, wherein the device comprises:

a data store, in which data sets with functional values are stored, which have been computed from the images of the cavity, wherein at least two data sets with functional values have been provided in respectively different data formats, wherein the data formats are chosen from the group consisting of a data table, a projection on to a 2D plane, or a grid network structure in the data store;

a data store, in which a uniform data format is stored;

a computing unit, which is adapted to convert data sets with functional values not provided in a uniform data format into the uniform format, and to compute the data sets present in the uniform format with one another in order to produce at least one result data set; and a screen suitable for displaying the result data set.

17. Device according to claim 16, wherein the device is configured to perform a method of evaluating images of a cavity in a human or an animal body, which have been acquired with one or more different medical imaging methods, wherein data sets with functional values, computed from said images, are used, the method comprising the steps of:

providing at least two data sets with functional values in different data formats, wherein the data formats are chosen from the group consisting of a data table, a projection on to a 2D plane, or a grid network structure;

providing a uniform data format;

converting a data set with functional values not made available in the uniform data format into the uniform data format;

Mathematically computing data sets present in the uniform data format with one another to generate at least one result data set; and representing the result data set.

* * * * *